United States Patent
Tran et al.

(10) Patent No.: US 10,362,991 B2
(45) Date of Patent: Jul. 30, 2019

(54) CONVERTIBLE BASKET CATHETER

(71) Applicant: Biosense Webster (Israel) Ltd., Yokneam (IL)

(72) Inventors: Paul Tran, San Gabriel, CA (US); Mario A. Solis, Rancho Cucamonga, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 275 days.

(21) Appl. No.: 15/090,435

(22) Filed: Apr. 4, 2016

(65) Prior Publication Data

US 2017/0281268 A1    Oct. 5, 2017

(51) Int. Cl.
*A61B 5/0492* (2006.01)
*A61B 18/14* (2006.01)
*A61B 5/00* (2006.01)
*A61B 5/042* (2006.01)
*A61B 17/00* (2006.01)
*A61B 18/00* (2006.01)

(52) U.S. Cl.
CPC .......... *A61B 5/6858* (2013.01); *A61B 5/0422* (2013.01); *A61B 5/6859* (2013.01); *A61B 18/1492* (2013.01); *A61B 2017/00044* (2013.01); *A61B 2018/00267* (2013.01); *A61B 2018/00351* (2013.01)

(58) Field of Classification Search
CPC . A61B 18/1492; A61B 5/0422; A61B 5/6858; A61B 5/6859
See application file for complete search history.

(56) References Cited

U.S. PATENT DOCUMENTS

| | | | |
|---|---|---|---|
| 4,660,571 A * | 4/1987 | Hess | A61B 5/0422 604/105 |
| 5,391,199 A | 2/1995 | Ben-Haim | |
| 5,722,401 A * | 3/1998 | Pietroski | A61B 5/0422 600/374 |
| 5,772,590 A | 6/1998 | Webster, Jr. | |
| 5,911,739 A | 6/1999 | Kordis et al. | |

(Continued)

FOREIGN PATENT DOCUMENTS

| | | |
|---|---|---|
| EP | 2201905 A1 | 6/2010 |
| WO | 96/05768 | 2/1996 |

OTHER PUBLICATIONS

European Search Report for European Patent Application No. 17164497.4, dated Aug. 28, 2017; 9 pages.

(Continued)

*Primary Examiner* — Lee S Cohen
(74) *Attorney, Agent, or Firm* — Dergosits & Noah LLP; Todd A. Noah

(57) ABSTRACT

This disclosure is directed to a catheter having a basket-shaped electrode assembly at the distal end of the catheter body formed from a plurality of spines with electrodes. The basket-shaped electrode assembly structural elements at the proximal and distal ends. The structural elements may maintain the spines in a desired spatial relationship with each other and/or may couple the distal ends of the spines to a pulling member. The basket-shaped electrode assembly has expanded arrangement in which the spines bow outwards and a collapsed arrangement in which the spines are arranged generally along a longitudinal axis of the catheter body.

19 Claims, 6 Drawing Sheets

(56) References Cited

U.S. PATENT DOCUMENTS

| | | | |
|---|---|---|---|
| 6,064,905 A | 5/2000 | Webster et al. | |
| 6,120,496 A * | 9/2000 | Whayne | A61B 18/1492 128/DIG. 26 |
| 6,165,169 A * | 12/2000 | Panescu | A61B 18/1492 606/1 |
| 6,239,724 B1 | 5/2001 | Doron et al. | |
| 6,332,089 B1 | 12/2001 | Acker et al. | |
| 6,484,118 B1 | 11/2002 | Govari | |
| 6,618,612 B1 | 9/2003 | Acker et al. | |
| 6,690,963 B2 | 2/2004 | Ben-Haim et al. | |
| 6,748,255 B2 * | 6/2004 | Fuimaono | A61B 5/0402 128/899 |
| 6,973,340 B2 | 12/2005 | Fuimaono et al. | |
| 8,364,234 B2 * | 1/2013 | Kordis | A61B 5/0422 600/372 |
| 8,588,885 B2 * | 11/2013 | Hall | A61B 5/0422 600/374 |
| 9,314,208 B1 * | 4/2016 | Altmann | A61B 5/6858 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2013/0172715 A1 | 7/2013 | Just et al. | |
| 2014/0364926 A1 | 12/2014 | Nguyen et al. | |
| 2015/0342491 A1 * | 12/2015 | Marecki | A61B 18/1492 600/374 |
| 2015/0342532 A1 | 12/2015 | Basu et al. | |
| 2016/0066990 A1 | 3/2016 | Kaplan et al. | |

OTHER PUBLICATIONS

U.S. Appl. No. 13/860,921, filed Apr. 11, 2013, entitled High Density Electrode Structure.

U.S. Appl. No. 14/063,477, filed Oct. 25, 2013, entitled Connection of Electrodes to Wires Coiled on a Core.

* cited by examiner

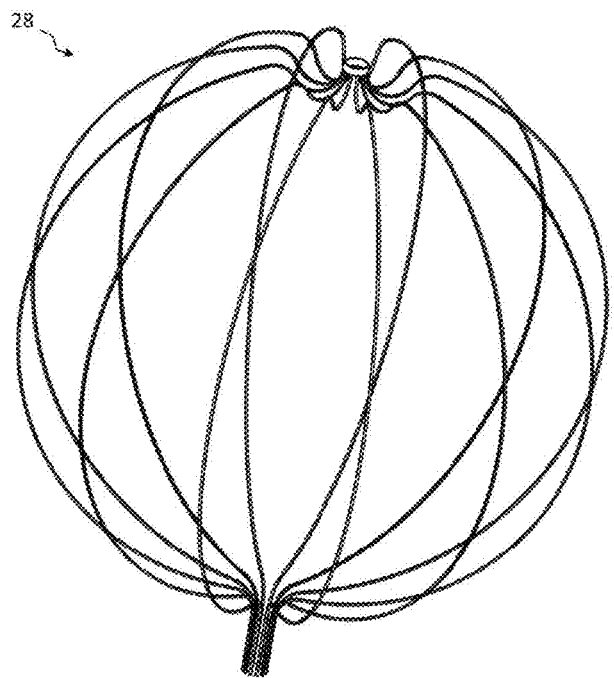
FIG. 2
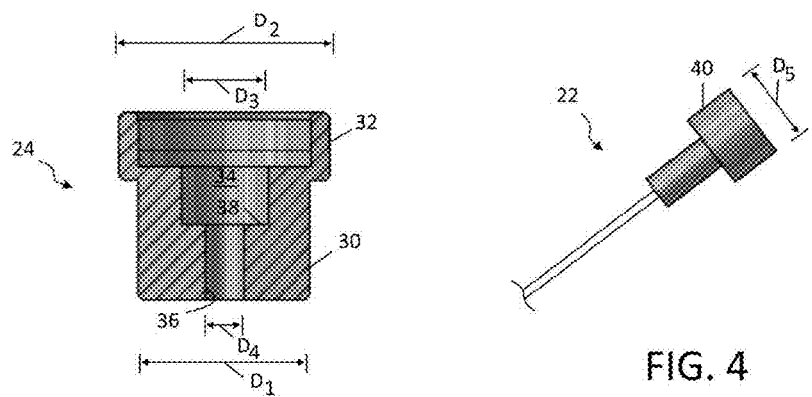
FIG. 3
FIG. 4

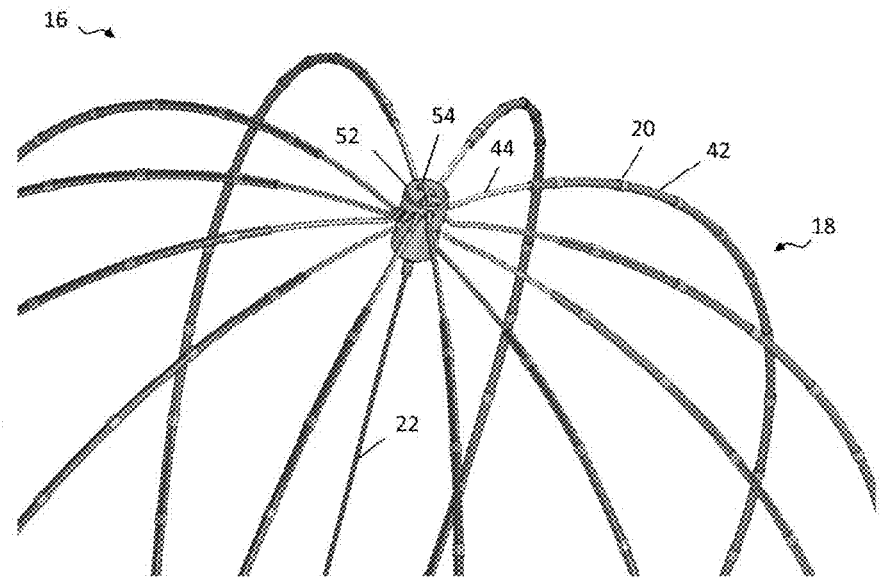
FIG. 8
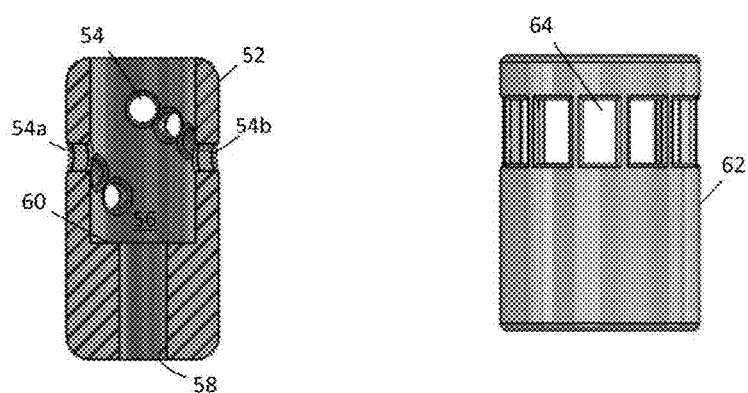
FIG. 9
FIG. 10

CONVERTIBLE BASKET CATHETER

FIELD OF THE PRESENT DISCLOSURE

This disclosure relates to electrophysiologic (EP) catheters for mapping and/or ablation in the heart, in particular, to structural elements to reliably deploy EP catheters within a patient.

BACKGROUND

Electrophysiology catheters are commonly-used for mapping electrical activity in the heart and/or for delivering energy to perform a therapeutic procedure. Various electrode designs are known for different purposes. In particular, catheters having basket-shaped electrode arrays are known and described, for example, in U.S. Pat. Nos. 5,772,590, 6,748,255 and 6,973,340, the entire disclosures of each of which are incorporated herein by reference.

Basket catheters typically have an elongated catheter body and a basket-shaped electrode assembly mounted at the distal end of the catheter body. The basket assembly has proximal and distal ends and comprises a plurality of spines connected at their proximal and distal ends. Each spine comprises at least one electrode. The basket assembly has an expanded arrangement wherein the spines bow radially outwardly and a collapsed arrangement wherein the spines are arranged generally along the axis of the catheter body. In some circumstances, the expanded arrangement may be achieved by proximally withdrawing a pulling member secured to the distal ends of the spines to decrease the relative longitudinal distance to the proximal ends of the spines to cause the outward bowing.

For diagnostic purposes, it is desirable that a basket assembly be capable of detecting in as few beats as possible, including a single beat, as much of the electrical function of the region in which the electrode assembly is deployed, such as the left or right atrium. To reliably achieve this goal, the basket should deploy into a specific configuration that positions the spines with a desired relative spacing to each other in order to obtain uniform coverage of the tissue in the region of interest with the electrodes carried by the spines. Similarly, when employing a basket catheter to deliver energy for a therapeutic procedure, such as tissue ablation, achieving a specific spine configuration when the basket assembly is deployed helps ensure that one or more of the electrodes carried by the spines are positioned at the intended treatment site.

Accordingly, it would be desirable to provide structural elements that control deployment of the spines to achieve a specific configuration when the basket assembly is expanded. Likewise, it would be desirable to provide a structural element at the distal end of the basket assembly that allows a pulling member to be readily secured to the distal ends of the spines. Further, it would be desirable to provide a structural element at the distal end to maintain relative radial spacing of the spines. Still further, it would be desirable to provide a structural element at the proximal end of the basket assembly to maintain relative radial spacing of the spines. The techniques of this disclosure as described in the following materials satisfy these and other needs.

SUMMARY

The present disclosure is directed to a catheter having an elongated catheter body with proximal and distal ends and at least one lumen therethrough. The catheter body has a basket-shaped electrode assembly at the distal end, which includes a plurality of spines having proximal ends connected by a proximal structural element and a distal structural element, each spine comprising a plurality of electrodes, wherein the basket-shaped electrode assembly has an expanded arrangement in which the spines bow radially outward and a collapsed arrangement in which the spines are arranged generally along a longitudinal axis of the catheter body.

In one aspect, the catheter has a pulling member with proximal and distal ends, the pulling member slidably disposed within the lumen and aligned with the longitudinal axis of the catheter body, such that the basket-shaped electrode assembly has the collapsed arrangement when the pulling member is at a most distal position along the longitudinal axis relative to the catheter body and wherein the basket-shaped electrode assembly has the expanded arrangement when the pulling member is proximal to the most distal position.

In one aspect, the distal structural element may be a cap configured to couple the pulling member to the distal ends of the plurality of spines. The cap may have an interior recess defining a shoulder that engages a stop at a distal end of the pulling member.

In one aspect, the spines may be a monolithic framework formed by a cut tube of material. For example, the tube of material may be a shape memory material.

In one aspect, the cap may have a proximal portion with an outer diameter and a distal portion with an outer diameter, wherein the outer diameter of the proximal portion is less than the outer diameter of the distal portion. The outer diameter of the proximal portion is sized to fit closely within an inner diameter of the tube of material.

In one aspect, opposing spines of the basket-shaped electrode assembly may be formed by a continuous loop member. For example, the loop member may be a shape memory material.

In one aspect, the cap may have opposing apertures through which the loop member passes. The opposing apertures may be a plurality of pairs of opposing apertures, wherein each pair is helically staggered with respect to adjacent apertures. Alternatively, the cap may have opposing windows through which the loop member passes.

In one aspect, the proximal structural element may be a collar disposed within the lumen of the catheter body. The collar may have a plurality of longitudinal channels distributed around an outer diameter of the collar, each channel configured to receive and secure a proximal end of a spine. Each channel may form a lumen with an inner diameter of the catheter body when the collar is disposed within the catheter body. The collar may have a first lumen configured to accommodate a pulling member. Alternatively or in addition, the collar may have a second lumen configured to conduct irrigation fluid to the basket-shaped electrode assembly. Alternatively or in addition, the collar may have a third lumen configured to secure a location sensor.

This disclosure is also directed to a method for treatment that may include providing a catheter with an elongated catheter body having proximal and distal ends and at least one lumen therethrough and a basket-shaped electrode assembly at the distal end of the catheter body, the basket-shaped electrode assembly comprising a plurality of spines having proximal ends connected by a proximal structural element and a distal structural element, each spine comprising a plurality of electrodes, advancing the distal end of the catheter with the basket-shaped electrode assembly to a desired region within a patient with the interconnected framework in a collapsed arrangement in which the spines are arranged generally along a longitudinal axis of the catheter body and causing the basket-shaped electrode assembly to assume an expanded arrangement in which the elements are positioned radially outwards from the longitudinal axis of the catheter body so that at least one electrode is in contact with tissue.

In one aspect, the method may include receiving electrical signals from the at least one electrode in contact with tissue.

In one aspect, the method may include delivering radio frequency energy to the at least one electrode in contact with tissue to form a lesion.

BRIEF DESCRIPTION OF THE DRAWINGS

Further features and advantages will become apparent from the following and more particular description of the preferred embodiments of the disclosure, as illustrated in the accompanying drawings, and in which like referenced characters generally refer to the same parts or elements throughout the views, and in which:

FIG. 2 is a schematic view of a framework of a basket-shaped electrode assembly formed from a cut tube, according to one embodiment.

FIG. 3 is a schematic cross section of a cap structural element for use with the framework of FIG. 2, according to one embodiment.

FIG. 4 is a schematic view of a distal end of a pulling member, according to one embodiment.

FIG. 8 is a detail view showing the connection between the cap and the framework of a basket-shaped electrode assembly formed by continuous loop members, according to one embodiment.

FIG. 9 is a schematic cross section of a cap structural element for use with a framework of continuous loop members, according to one embodiment.

FIG. 10 is a schematic cross section of another cap structural element configuration for use with a framework of continuous loop members, according to one embodiment.

DETAILED DESCRIPTION

Figure 1:
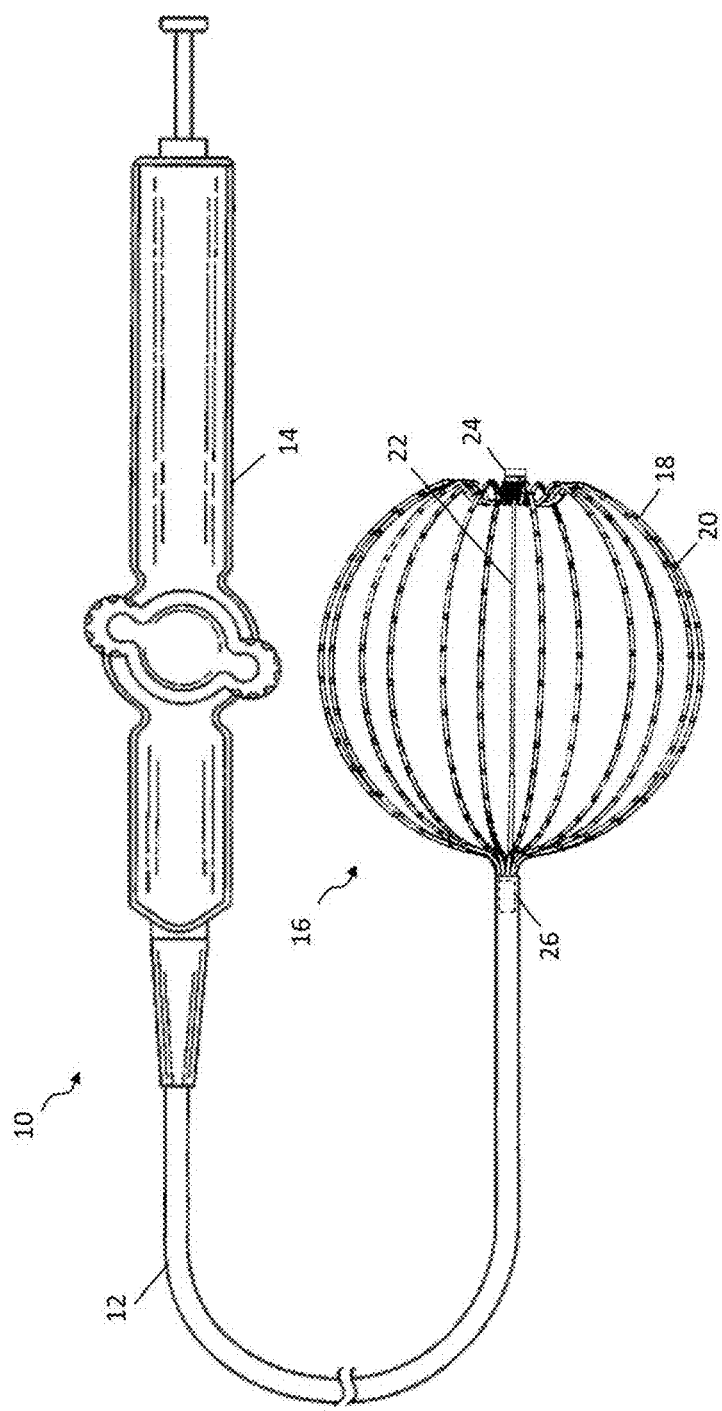
FIG. 1 is a top plan view of a basket-shaped electrode assembly catheter, according to one embodiment.

At the outset, it is to be understood that this disclosure is not limited to particularly exemplified materials, architectures, routines, methods or structures as such may vary. Thus, although a number of such options, similar or equivalent to those described herein, can be used in the practice or embodiments of this disclosure, the preferred materials and methods are described herein.

It is also to be understood that the terminology used herein is for the purpose of describing particular embodiments of this disclosure only and is not intended to be limiting.

The detailed description set forth below in connection with the appended drawings is intended as a description of exemplary embodiments of the present disclosure and is not intended to represent the only exemplary embodiments in which the present disclosure can be practiced. The term "exemplary" used throughout this description means "serving as an example, instance, or illustration," and should not necessarily be construed as preferred or advantageous over other exemplary embodiments. The detailed description includes specific details for the purpose of providing a thorough understanding of the exemplary embodiments of the specification. It will be apparent to those skilled in the art that the exemplary embodiments of the specification may be practiced without these specific details. In some instances, well known structures and devices are shown in block diagram form in order to avoid obscuring the novelty of the exemplary embodiments presented herein.

For purposes of convenience and clarity only, directional terms, such as top, bottom, left, right, up, down, over, above, below, beneath, rear, back, and front, may be used with respect to the accompanying drawings. These and similar directional terms should not be construed to limit the scope of the disclosure in any manner.

Unless defined otherwise, all technical and scientific terms used herein have the same meaning as commonly understood by one having ordinary skill in the art to which the disclosure pertains.

Finally, as used in this specification and the appended claims, the singular forms "a, "an" and "the" include plural referents unless the content clearly dictates otherwise.

Certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or 'map' this type of electrical activity, it is desirable to obtain the 'picture' as quickly as possible, such as within one heartbeat. In other words, all the points of the map or picture may be obtained simultaneously within one-tenth of a second. According to the techniques of this disclosure, a basket-shaped electrode assembly may conform more closely to the anatomy of the patient's heart in order to accurately map this electrical activity. By employing structural elements at the proximal and distal ends of the basket-shaped electrode assembly, the spines may be deployed reliably into a desired, specific configuration.

As shown in FIG. 1, the catheter 10 comprises an elongated catheter body 12 having proximal and distal ends and a control handle 14 at the proximal end of the catheter body, with a basket-shaped electrode assembly 16 having a plurality of spines 18, each carrying multiple electrodes 20, mounted at the distal end of the catheter body 12. The catheter body 12 comprises an elongated tubular construction having a single, axial or central lumen (not shown), but can optionally have multiple lumens if desired. To enable accurate mapping of electrical signals, for example to detect most or substantially all of the electrical function of the right or left atrium in as little as a single heartbeat, some embodiments may provide an array of electrodes with a relatively high density. As such, numbers of spines 18 employed may be eight, ten, twelve or any other suitable number. Spines 18 may be evenly or unevenly distributed radially. Further, each spine 18 may include multiple electrodes 20, such as at least ten and up to approximately 16 electrodes per spine. In other applications, fewer numbers of spines and/or electrodes may be employed as desired. Further, the electrodes may be evenly distributed along each spine or may be skewed proximally, centrally or distally to facilitate analysis of the measured electrical signals or to access desired regions of the patient's anatomy. In some embodiments, one or more of electrodes 20 may be configured to deliver radio frequency energy to ablate tissue adjacent the electrode.

The catheter body 12 is flexible, i.e., bendable, but substantially non-compressible along its length. The catheter body 12 can be of any suitable construction and made of any suitable material. One construction comprises an outer wall made of polyurethane or PEBAX® (polyether block amide). The outer wall comprises an imbedded braided mesh of stainless steel or the like to increase torsional stiffness of the catheter body 12 so that, when the control handle 14 is rotated, the distal end of the catheter body will rotate in a corresponding manner. The outer diameter of the catheter body 12 is not critical, but generally should be as small as possible and may be no more than about 10 french depending on the desired application. Likewise, the thickness of the outer wall is not critical, but may be thin enough so that the central lumen can accommodate a pulling member wire, lead wires, sensor cables and any other wires, cables or tubes. If desired, the inner surface of the outer wall is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

The basket-shaped electrode assembly 16 may also include a pulling member 22 that is generally coaxial with the catheter body 12 and extends from the proximal end of catheter body 12 through the central lumen and is attached to a structural element, such as cap 24, to couple pulling member 22 to the distal ends of spines 18. The pulling member 22 is afforded longitudinal movement relative to the catheter body so that it can move the distal ends of the spines 18 proximally relative to the catheter body 12 to radially expand the electrode assembly. In some embodiments, spines 18 may have a preshaped expanded configuration that they assume when unconstrained, and do not require a pulling member. The proximal ends of spines 18 may be received by another structural element disposed within catheter body 12, such as collar 26 as schematically indicated in FIG. 1. As will be described in further detail below, collar 26 may secure and maintain the proximal ends of spines 18 in a desired radial configuration with respect to each other.

Since the proximal ends of spines 18 are secured to the catheter body 12 by collar 26, the distance between the distal and proximal ends of spines 18 shortens when they bow outwards into an expanded arrangement, which may be associated with relative movement of pulling member 22 in the proximal direction. Alternatively or in addition, spines 18 may include a material as described below that facilitates assuming the expanded arrangement, such as a shape memory material, so that pulling member 22 aids the transition between the expanded and collapsed arrangements or is unnecessary. In an embodiment, the pulling member 22 may comprise a wire or hypotube formed from a suitable shape memory material, such as a nickel titanium alloy as described below. As will be appreciated, different relative amounts of movement of the pulling member 22 along the longitudinal axis may affect the degree of bowing, such as to enable the spines 18 to exert greater pressure on the atrial tissue for better contact between the tissue and the electrodes on the spines. Thus, a user can modify the shape of the electrode assembly by adjusting the distance pulling member 22 is withdrawn when basket-shaped electrode assembly 16 assumes an expanded arrangement.

A range of travel of pulling member 22 from its most distal location to a relatively more proximal location corresponds to deflection of basket-shaped electrode assembly 16 from a collapsed arrangement to an expanded arrangement having the generally spherical shape shown in FIG. 1. When in the collapsed arrangement, the spines may be constrained, such as by a guiding sheath, and may be deflected from the collapsed arrangement to the first expanded deployed configuration by withdrawing the guiding sheath and imparting sufficient force to pulling member 22. As will be appreciated, in the collapsed arrangement, spines 18 assume a generally linear alignment with the catheter body 12 to minimize the outer diameter for insertion within and withdrawal from the patient. In expanding to an expanded arrangement, spines 18 of basket-shaped electrode assembly 16 bow outwards. When positioned at a desired location within a patient, assuming an expanded arrangement may bring electrodes 20 into contract or closer proximity with the walls of the chamber or other region in which basket-shaped electrode assembly 16 is positioned. The overall size of basket-shaped electrode assembly 16 may be selected based on the patient's anatomy to provide a close fit to the area of the patient being investigated or treated, such as the right or left atria. In some embodiments, pulling member 22 may be coupled to an actuator on control handle 14, which may be a sliding lever, a rotating knob or any other suitable implementation. As such, the actuator may be used to adjust the relative longitudinal position of pulling member 22 and in particular may be configured adjust the position of pulling member 22 to achieve one or more desired expanded arrangements of basket-shaped electrode assembly 16.

Basket-shaped electrode assembly 16 may be constructed by employing a framework of a suitable substrate material. In one aspect, a shape memory material may be used to aid assuming the expanded and collapsed arrangements. For example, nickel-titanium alloys known as nitinol may be used. At body temperature, nitinol wire is flexible and elastic and, like most metals, nitinol wires deform when subjected to minimal force and return to their shape in the absence of that force. Nitinol belongs to a class of materials called Shaped Memory Alloys (SMA) that have interesting mechanical properties beyond flexibility and elasticity, including shape memory and superelasticity which allow nitinol to have a "memorized shape" that is dependent on its temperature phases. The austenite phase is nitinol's stronger, higher-temperature phase, with a simple cubic crystalline structure. Superelastic behavior occurs in this phase (over a 50°-60° C. temperature spread). Correspondingly, the martensite phase is a relatively weaker, lower-temperature phase with a twinned crystalline structure. When a nitinol material is in the martensite phase, it is relatively easily deformed and will remain deformed. However, when heated above its austenite transition temperature, the nitinol material will return to its pre-deformed shape, producing the "shape memory" effect. The temperature at which nitinol starts to transform to austenite upon heating is referred to as the "As" temperature. The temperature at which nitinol has finished transforming to austenite upon heating is referred to as the "Af" temperature. Accordingly, basket-shaped electrode assembly 16 when formed from such materials may have a three dimensional shape that can be easily collapsed to be fed into a guiding sheath and then readily returned to its expanded shape memory configuration upon delivery to the desired region of the patient upon removal of the guiding sheath and/or actuation of pulling member 22.

In one exemplary embodiment, a framework 28 may be formed from a nitinol hypotube by laser cutting or other similar techniques, to provide a monolithic framework as shown in FIG. 2. Depending on the embodiment, a 3 mm tube having a wall thickness of approximately 8 to 9 mil may be used. Alternative embodiments may employ other materials do not necessarily have shape memory characteristics, but have sufficient resilience to assume the expanded and collapsed arrangements, including metallic materials such as stainless steel or polymeric materials such as polyetheretheketone (PEEK).

An embodiment of cap 24 that is adapted for use with a framework 28 formed from a cut tube is shown in cross section in FIG. 3. Cap 24 may have a proximal portion 30 having a diameter $D_1$ that is sized to fit closely within the inner diameter of the tube used to construct framework 28, a distal portion of which may be left intact. Further, cap 24 may have a distal portion 32 having a diameter $D_2$ greater than $D_1$, for example approximately the outer diameter of the tube used to construct framework 28 but at the least greater than the inner diameter of the tube. Accordingly, the proximal portion 30 of cap 24 may be disposed within and secured to the distal end of framework 28, within the intact, uncut portion. Cap 24 also includes an interior recess 34 having an inner diameter $D_3$. A lumen 36 extends from recess 34 to the proximal end of cap 24. Lumen 36 has an inner diameter $D_4$ that, in cooperation with the inner diameter $D_3$ of recess 34, defines a shoulder 38 that interfaces with pulling member 22. As shown in FIG. 4, the distal end of pulling member 22 may have a stop 40 with an outer diameter $D_5$ that fits within inner diameter $D_3$ of recess 34 but is greater than the inner diameter $D_4$ of lumen 36 so that stop 40 engages shoulder 38. Accordingly, pulling member 22 may readily be secured to cap 24 and stop 40 provides mechanical interaction with shoulder 38 so that proximal motion of pulling member 22 reliably effects a corresponding proximal motion of cap 24 and the distal ends of spines 18 to cause the outward bowing as basket-shaped electrode assembly 16 assumes an expanded arrangement. Stop 40 may be retained within recess 34 by an suitable technique, including adhesively.

Figure 5:
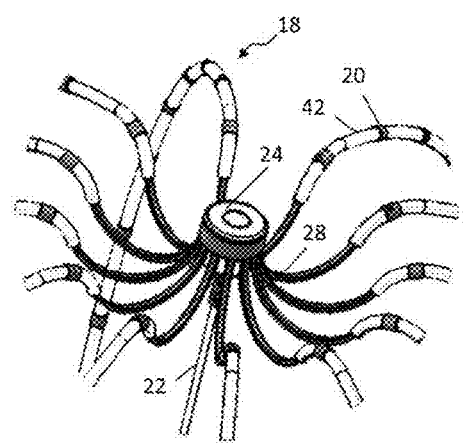
FIG. 5 is a detail view showing the interaction between the cap and the framework of a basket-shaped electrode assembly, according to one embodiment.

A detailed view of the distal end of basket-shaped electrode assembly 16 is shown FIG. 5 that illustrates the connection between cap 24 and the tubular distal end of framework 28. As shown in this view, the spines 18 have a substrate formed by framework 28 and may include a non-conductive covering 42, which may comprise a biocompatible plastic tubing, such as polyurethane or polyimide tubing, on which electrodes 20 are mounted. In embodiments that feature a polymeric framework, the non-conductive covering may be omitted. The configuration shown in FIG. 5 employs distal portions of spines 18 that exhibit a concave configuration, positioned generally within a radius of curvature defined by the adjacent proximal portion. This invaginated design keeps the top of basket-shaped electrode assembly 16 approximately flush with the outer curvature for safety reasons, by presenting a relatively blunt and atraumatic surface. Further, an electrode 20 may be positioned at the inflexion point where the concave distal portion 32 transitions to the convex portion proximal to it to provide coverage in the polar region of basket-shaped electrode assembly 16. Spines 18 may be provided with varying degrees of curvature in order to more closely conform to the anatomy of the patient.

Figures 6, 7:
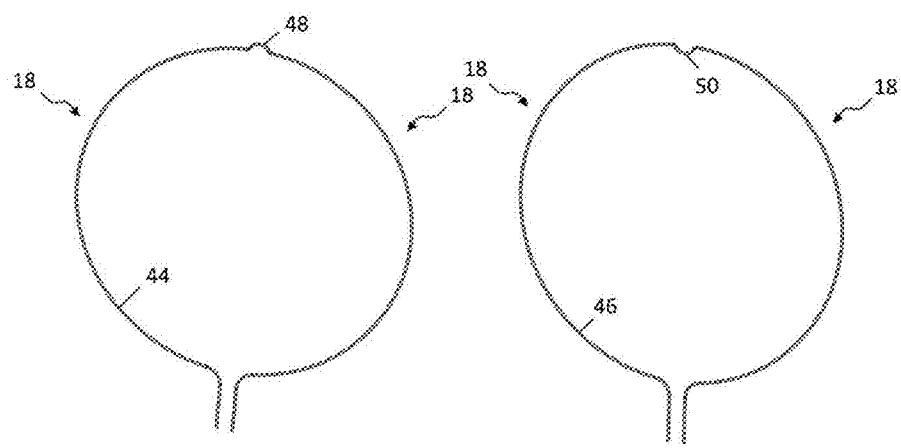
FIG. 6 is a schematic view of a continuous loop member that forms opposing spines, according to an embodiment.
FIG. 7 is a schematic view of another continuous loop member that forms opposing spines, according to an embodiment.

In another exemplary embodiment, the framework of basket-shaped electrode assembly 16 may employ a continuous loop of material to form two opposing spines 18. For example, FIGS. 6 and 7 show loop members 44 and 46, respectively, each of which form opposing spines 18. As shown in FIG. 6, loop member 44 may have a convex distal region 48 generally formed outside the radius of curvature of loop member 44. Alternatively, as shown in FIG. 7, loop member 46 may have a concave distal region 50 generally formed inside the radius of curvature of loop member 46. Convex region 48 and/or concave region 50 may be employed to reduce interference with other loop members that may be stacked to form a complete basket-shaped electrode assembly 16 having a desired number of spines 18. The radii of curvature for convex region 48 and/or concave region 50 for each loop member may be adjusted as necessary to provide clearance with respect to other loop members. Loop members 44 and/or 46 may comprise any suitably resilient material, such as those discussed above with respect to framework 28. In some embodiments, nitinol or other shape memory materials may be used. Further, loop members 44 and/or 46 may have a round, oval, square or other rectangular profile as desired.

A partial view of an embodiment of basket-shaped electrode assembly 16 formed from loop members 44 is shown in FIG. 8. Similar to the other embodiments described above, loop members 44 may have a non-conductive covering 42 upon which electrodes 20 are disposed. A structural element for coupling the distal ends of spines 18 to pulling member 22 is provided in the form of cap 52, which has a plurality of opposing apertures 54 through which loop members 44 are routed. In yet other embodiments, each spine 18 may be formed by individual members, each of which may be secured at the distal end by an aperture 54 of cap 52. In each of these embodiments, apertures 54 help maintain the distal ends of spines 18 in a desired radial spacing with respect to each other.

A detailed, cross sectional view of cap 52 is shown in FIG. 9. Each pair of opposing apertures 54, such as apertures 54a and 54b, may be helical staggered around the radius of cap 52 to provide interference between the loop members 44 (not shown in this view) routed through them. Apertures 54 may be shaped to accommodate the profile of loop members 44 and/or 46, such as by having a round, oval, square or rectangular configuration. Cap 52 may also feature a recess 56 and lumen 58 that cooperate to form shoulder 60. These aspects of cap 52 may be sized as described above with regard to cap 24 to secure stop 40 of pulling member 22. An alternative embodiment is shown in the form of cap 62 as shown in FIG. 10, which employs a plurality of windows 64 to provide greater clearance for loop members 44 and/or 46. Although not shown in this view, cap 62 may also have an interior shoulder similar to the other embodiments for engaging stop 40 of pulling member 22.

Figure 11:
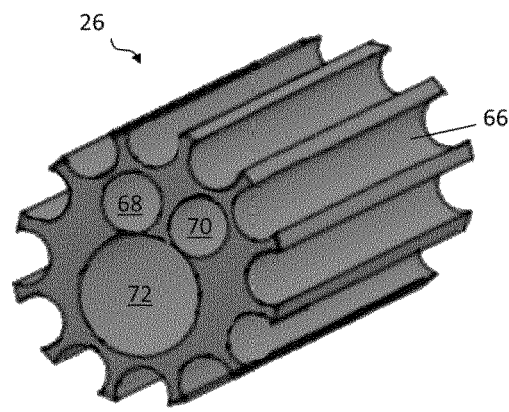
FIG. 11 is a schematic elevational view of a collar structural element, according to one embodiment.

As noted above, the proximal ends of spines 18, whether cut from a tube as in framework 28 or comprising opposing ends of loop members 44 and/or 46, may be received and secured by a structural element such as collar 26, which is shown in FIG. 11. Collar 26 may have a generally cylindrical shape, sized to fit closely within catheter body 12. A plurality of longitudinal channels 66 are distributed radially around the cylindrical body of collar 26. Each channel 66 may be sized to receive and secure a proximal end of one spine 18. Channels 66 may form lumens in conjunction with the surface of the inner diameter of catheter body 12 when collar 26 is disposed within the catheter body and spines 18 may be secured by the channels in any suitable manner, including adhesively. As will be appreciated, channels 66 maintain the proximal ends of spines 18 in a desired radial spacing with respect to each other. Although shown as being evenly distributed, in some embodiments the channels may be unevenly distributed to produce a corresponding radial distribution of spines 18 if desired. Collar 26 may have a first lumen 68 that extends from the proximal end to the distal end, through which pulling member 44 may pass. Collar 26 may have a second lumen 70 that also extends from the proximal end to the distal end, to supply a suitable irrigation fluid, such as heparinized saline, to the basket-shaped electrode assembly 16. A fitting (not shown) in the control handle 14 may be provided to conduct irrigation fluid from a suitable source or pump into a lumen or tubing extending through catheter body 12 that is in communication with lumen 70. Collar 26 may have a third lumen 72 that terminates within the body of collar 26 to secure and position a location sensor (not shown in this figure) that may be used to help determine the location of basket-shaped electrode assembly 16 within a patient as described in further detail below.

Figure 12:
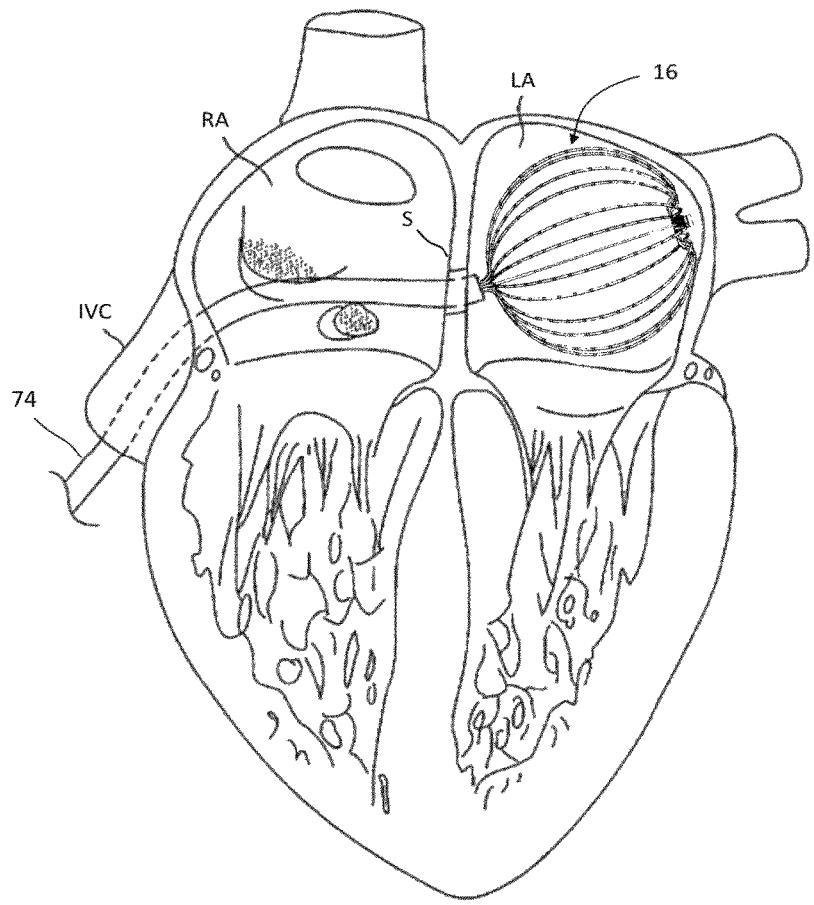
FIG. 12 is a schematic view of a basket-shaped electrode assembly in an expanded arrangement within the left atrium, according to one embodiment.

In one aspect, an electrophysiologist may introduce a guiding sheath, guidewire and dilator into the patient, as is generally known in the art. Examples of suitable guiding sheaths for use in connection with the inventive catheter are the PREFACE™ Braided Guiding Sheath (commercially available from Biosense Webster, Inc., Diamond Bar, Calif.) and the DiRex™ Guiding Sheath (commercially available from BARD, Murray Hill, N.J.). The guidewire is inserted, the dilator is removed, and the catheter is introduced through the guiding sheath whereby the guidewire lumen in the pulling member permits the catheter to pass over the guidewire. In one exemplary procedure as depicted in FIG. 12, the catheter is first introduced to the right atrium (RA) via the inferior vena cava (IVC), where it passes through the septum (S) in order to reach the left atrium (LA).

As will be appreciated, guiding sheath 74 covers the spines 18 of the basket-shaped electrode assembly 16 in a collapsed position so that the entire catheter can be passed through the patient's vasculature to the desired location. The pulling member 22 may be positioned distally of the catheter body to allow the spines of the assembly to be flattened while the assembly is passed through the guiding sheath. Once the distal end of the catheter reaches the desired location, e.g., the left atrium, the guiding sheath is withdrawn to expose the basket-shaped electrode assembly 16. The pulling member 22 is drawn proximally or otherwise manipulated so that the spines 18 flex outwardly between the distal and proximal junctions. With the basket-shaped electrode assembly 16 radially expanded, electrodes 20 contact atrial tissue.

When the basket-shaped electrode assembly 16 is deployed into its expanded arrangement, the electrophysiologist may map local activation time and/or ablate using electrodes 20, which can guide the electrophysiologist in diagnosing and providing therapy to the patient. The catheter may include one or more reference ring electrodes mounted on the catheter body and/or one or more reference electrodes may be placed outside the body of the patient. By using the inventive catheter with the multiple electrodes on the basket-shaped electrode assembly, the electrophysiologist can obtain a true anatomy of a cavernous region of the heart, including an atrium, by measuring less points than with traditional catheters, allowing a more rapid mapping of the region.

In a further aspect, each spine 18 may include cabling with built-in or embedded lead wires for the electrodes 20 carried by the spine as described in U.S. application Ser. No. 13/860,921, filed Apr. 11, 2013, entitled HIGH DENSITY ELECTRODE STRUCTURE, and U.S. application Ser. No. 14/063,477, filed Oct. 25, 2013, entitled CONNECTION OF ELECTRODES TO WIRES COILED ON A CORE, the entire disclosures of which are hereby incorporated by reference.

Figure 13:
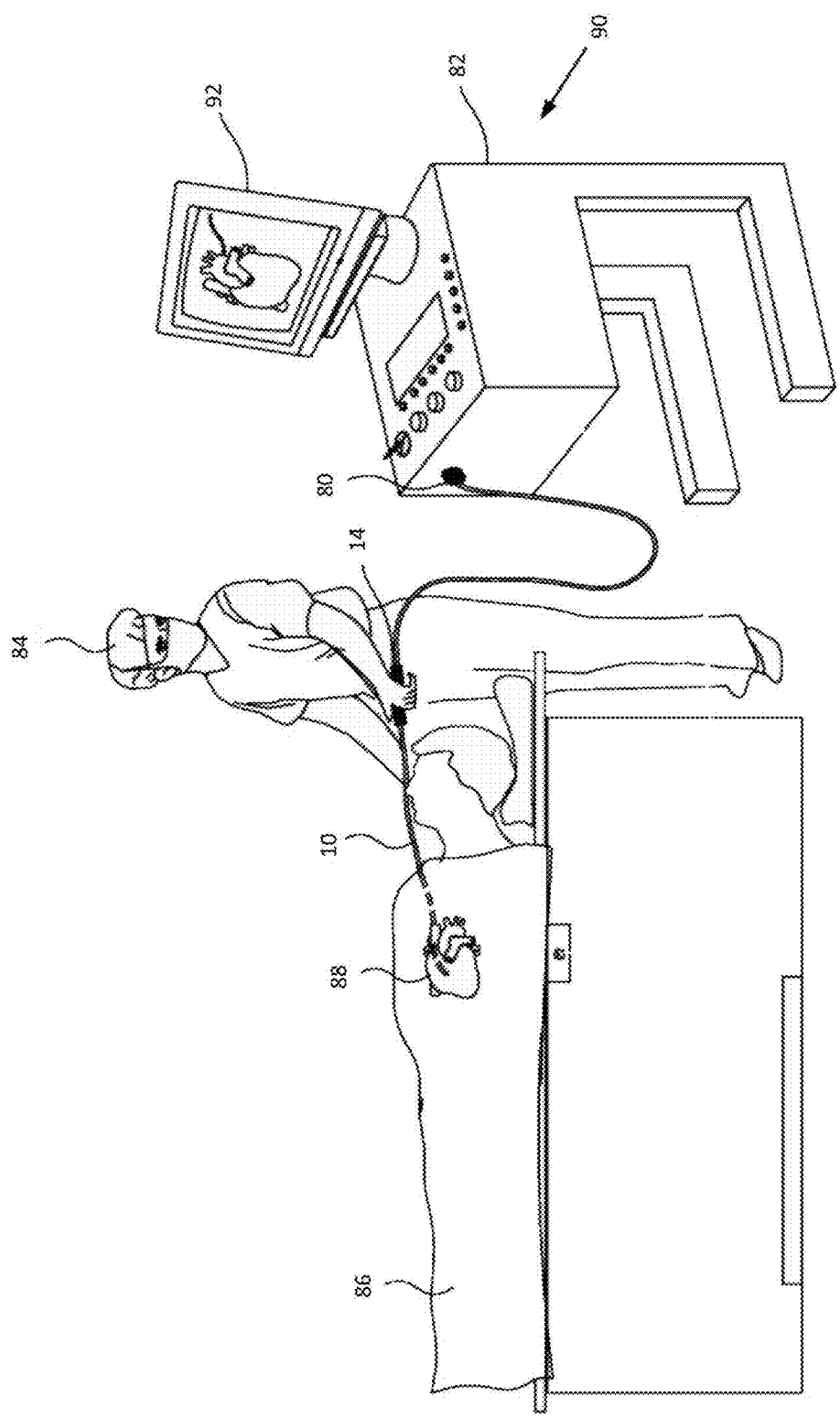
FIG. 13 is a schematic illustration of an invasive medical procedure using a basket-shaped electrode assembly, according to one embodiment.

To help illustrate use of the basket-shaped electrode assembly 16, FIG. 13 is a schematic depiction of an invasive medical procedure, according to an embodiment. Catheter 10, with the basket-shaped electrode assembly 16 (not shown in this view) at the distal end may have a connector 80 at the proximal end for coupling the wires from their respective electrodes 20 (not shown in this view) to a console 82 for recording and analyzing the signals they detect. An electrophysiologist 84 may insert the catheter 10 into a patient 86 in order to acquire electropotential signals from the heart 88 of the patient. The professional uses the control handle 14 attached to the catheter in order to perform the insertion. Console 82 may include a processing unit 90 which analyzes the received signals, and which may present results of the analysis on a display 92 attached to the console. The results are typically in the form of a map, numerical displays, and/or graphs derived from the signals.

In a further aspect, the processing unit 90 may also receive signals from one or more location sensors provided near a distal end of the catheter 10 adjacent the basket-shaped electrode assembly 16, such as by being secured with lumen 72 of collar 26 as described above. The sensor(s) may each comprise a magnetic-field-responsive coil or a plurality of such coils. Using a plurality of coils enables six-dimensional position and orientation coordinates to be determined. The sensors may therefore generate electrical position signals in response to the magnetic fields from external coils, thereby enabling processor 90 to determine the position, (e.g., the location and orientation) of the distal end of catheter 10 within the heart cavity. The electrophysiologist may then view the position of the basket-shaped electrode assembly 16 on an image the patient's heart on the display 92. By way of example, this method of position sensing may be implemented using the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference. As will be appreciated, other location sensing techniques may also be employed. If desired, at least two location sensors may be positioned proximally and distally with respect to electrode array assembly 16. The coordinates of the distal sensor relative to the proximal sensor may be determined and, with other known information pertaining to the configuration of basket-shaped electrode assembly 16, used to find the positions of each of the electrodes 20.

The preceding description has been presented with reference to presently disclosed embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising an elongated catheter body having proximal and distal ends and at least one lumen therethrough and a basket-shaped electrode assembly at the distal end of the catheter body, the basket-shaped electrode assembly comprising a plurality of spines having proximal ends connected by a proximal structural element and distal ends connected by a distal structural element, each spine comprising a plurality of electrodes, wherein the basket-shaped electrode assembly has an expanded arrangement in which the spines bow radially outward and a collapsed arrangement in which the spines are arranged generally along a longitudinal axis of the catheter body, a pulling member having proximal and distal ends, the pulling member slidably disposed within the lumen and aligned with the longitudinal axis of the catheter body, such that the basket-shaped electrode assembly has the collapsed arrangement when the pulling member is at a most distal position along the longitudinal axis relative to the catheter body and wherein the basket-shaped electrode assembly has the expanded arrangement when the pulling member is proximal to the most distal position, wherein the distal structural element comprises a cap configured to couple the pulling member to the distal ends of the plurality of spines, the cap having an interior recess defining a shoulder that engages a stop at a distal end of the pulling member, the shoulder positioned proximal to the distal ends of the plurality of spines.

2. The catheter of claim 1, wherein spines comprise a monolithic framework formed by a cut tube of material.

3. The catheter of claim 2, wherein tube of material comprises a shape memory material.

4. The catheter of claim 2, wherein the cap has a proximal portion with an outer diameter and a distal portion with an outer diameter, wherein the outer diameter of the proximal portion is less than the outer diameter of the distal portion.

5. The catheter of claim 4, wherein the outer diameter of the proximal portion is sized to fit closely within an inner diameter of the tube of material.

6. The catheter of claim 1, wherein opposing spines are formed by a continuous loop member.

7. The catheter of claim 6, wherein the loop member comprises a shape memory material.

8. The catheter of claim 6, wherein the cap has opposing apertures through which the loop member passes.

9. The catheter of claim 8, further comprising a plurality of pairs of opposing apertures, wherein each pair is helically staggered with respect to adjacent apertures.

10. The catheter of claim 6, wherein the cap has opposing windows through which the loop member passes.

11. The catheter of claim 1, wherein the proximal structural element comprises a collar disposed within the lumen of the catheter body.

12. The catheter of claim 11, wherein the collar has a plurality of longitudinal channels distributed around an outer diameter of the collar, each channel configured to receive and secure a proximal end of a spine.

13. The catheter of claim 12, wherein each channel forms a lumen with an inner diameter of the catheter body when the collar is disposed within the catheter body.

14. The catheter of claim 11, wherein the collar comprises a first lumen configured to accommodate a pulling member.

15. The catheter of claim 11, wherein the collar comprises a second lumen configured to conduct irrigation fluid to the basket-shaped electrode assembly.

16. The catheter of claim 11, wherein the collar comprises a third lumen configured to secure a location sensor.

17. A method for treatment comprising:
providing a catheter comprising an elongated catheter body having proximal and distal ends and at least one lumen therethrough and a basket-shaped electrode assembly at the distal end of the catheter body, the basket-shaped electrode assembly comprising a plurality of spines having proximal ends connected by a proximal structural element and distal ends connected by a distal structural element, each spine comprising a plurality of electrodes, a pulling member having proximal and distal ends, the pulling member slidably disposed within the lumen and aligned with a longitudinal axis of the catheter body, such that the basket-shaped electrode assembly has a collapsed arrangement when the pulling member is at a most distal position along the longitudinal axis relative to the catheter body and wherein the basket-shaped electrode assembly has an expanded arrangement when the pulling member is proximal to the most distal position, wherein the distal structural element comprises a cap configured to couple the pulling member to the distal ends of the plurality of spines, the cap having an interior recess defining a shoulder that engages a stop at a distal end of the pulling member, the shoulder positioned proximal to the distal ends of the plurality of spines;
advancing the distal end of the catheter with the basket-shaped electrode assembly to a desired region within a patient with the plurality of spines in a collapsed arrangement in which the spines are arranged generally along a longitudinal axis of the catheter body; and
causing the basket-shaped electrode assembly to assume an expanded arrangement in which the elements are positioned radially outwards from the longitudinal axis of the catheter body so that at least one electrode is in contact with tissue.

18. The method of claim 17, further comprising receiving electrical signals from the at least one electrode in contact with tissue.

19. The method of claim 17, further comprising delivering radio frequency energy to the at least one electrode in contact with tissue to form a lesion.

* * * * *